US00PP11899P2

(12) United States Plant Patent
Jessel, Jr.

(10) Patent No.: US PP11,899 P2
(45) Date of Patent: Jun. 5, 2001

(54) CARNATION PLANT NAMED 'CFPC SELENA'

(75) Inventor: Walter H. Jessel, Jr., Gonzales, CA (US)

(73) Assignee: California Florida Plant Co LP, Salinas, CA (US)

( * ) Notice: Subject to any disclaimer, the term of this patent is extended or adjusted under 35 U.S.C. 154(b) by 0 days.

(21) Appl. No.: 09/181,005

(22) Filed: Oct. 28, 1998

(51) Int. Cl.[7] ..... A01H 5/00
(52) U.S. Cl. ..... Plt./278
(58) Field of Search ..... Plt./278, 277, 282, Plt./283

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new variety of carnation plant producing bright crimson flowers.

1 Drawing Sheet

1

BACKGROUND OF THE INVENTION

The present invention relates to a new and distinct variety of carnation plant which was discovered by me as a natural branch mutation in a controlled planting of 'CFPC Debutante'. The varietal denominator of the new variety is 'CFPC Selena'.

SUMMARY OF THE INVENTION

Among the novel characteristics possessed by the new variety which distinguishes it is bright crimson flowers. When grown under glass in 4¼ inch pots in Salinas, Calif., pinched plants are about 6¾ inches tall and flowers are about 1¾ inches average diameter with a ¾ inch crown (average). Foliage is about 3½ inches long and about ⅜ inches wide. The new variety is mainly grown under greenhouse conditions but can be transplanted into a garden environment or patio container outdoors if protected from direct sun, in planting such as by walls or near shaded areas. It is expected that with regular watering and feeding, new blooms will grow and finish all year round.

Asexual reproduction by propagation by side shoot cuttings of the new variety as performed in Salinas, Calif., shows that the foregoing and other distinguishing characteristics come true to form and are established and transmitted through succeeding propagations.

COMPARISON WITH PARENT

The new variety differs from its parent'CFPC Debutante' (unpatented) in having different flower color. The average crop time of the new variety is about 16 to 18 weeks in winter and about 12 to14 weeks in late Spring and Summer for finishing.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

2

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypical expression may deviate from the description depending on environmental, seasonal and cultural conditions.

The information provided herein is based on observations of plants grown inside commercial greenhouses at Salinas, Calif. The height of plant and flower and foliage size are established as an average using standard commercial cultural practices.

Classification:
*Botanical.*—*Dianthus caryophyllus.*
*Commercial.*—Carnation, greenhouse type, suitable for production as a pot spray.

1. Plant:
*Height.*—About 6¾ inches.
*Growing habit.*—Herbaceous, semi-upright.
*Blooming habit.*—As a spray, of about 2 to 3 blooms per spray.
*Blooming season.*—Year round in green house.
*Rooting time.*—About 17 days.
*Disease resistance.*—Good, typical of carnations.

2. Foliage:
*Color.*—Upper side: Near 138A. Lower side: Near 137D.
*Size.*—About 3½ inches long×⅜ inches wide.
*Quantity.*—Numerous.
*Shape.*—Lanceolate.
*Texture.*—Smooth.
*Ribs.*—Central, Keeled.
*Arrangement.*—Bi-lateral along stem.
*Stem color.*—Near 137D.
*Pedicel.*—Near 137D.

3. Bud:
*Shape.*—Ovoid.
*Color.*—Near 138B.
*Length.*—About 1 inch.
*Diameter.*—About ⅜ inch.

4. Calyx:

There is no bursting/splitting of the calyx observed under growing conditions in Salinas, Calif.

*Number of bracts.*—About 5.

*Length.*—About ¾ inch.

*Width.*—About 5/16 inch.

*Color.*—Outside — 138B. Inside — 139D.

5. Bloom:

*Shape.*—Round.

*Size.*—Diameter average: About 1¾ inches. Depth average: About ¾ inch.

*Borne.*—Terminally.

*Color.*—General tonality: Crimson Red. Upper side: Near 53B. Lower side: Near 53B. Center: Near 53B. Outer petals: Near 53B.

*Fragrance.*—Very slight.

*Margin.*—Crimped.

*Lastingness.*—About 1 week after cutting.

6. Petals:

*Number.*—About 40.

*Outer petals.*—Length: About 1⅞ inches. Width: About ¾ inches.

*Central petals.*—Length: About 1¼ inches. Width: About ¼ inch.

*Texture.*—Smooth.

*Form.*—Fan shaped.

*Appearance.*—Shiny.

7. Reproductive organs:

*Stamens.*—None (male sterile).

*Pistil.*—Number: One, 3 lobed. Color: Mature, whiter than 155D, immature with tinged 53B. Length: About 1¼ inches.

*Stigma.*—Number: About 3. Color: Whiter than 155D, tinged 53B when immature.

*Ovary.*—Shape: Conical. Color: Base — near 155D. Body — Near 145B. Apex — Near 18C.

*Fertility.*—Good. Male: None.

I claim:

1. A new and distinct carnation plant of the variety substantially as shown and described.

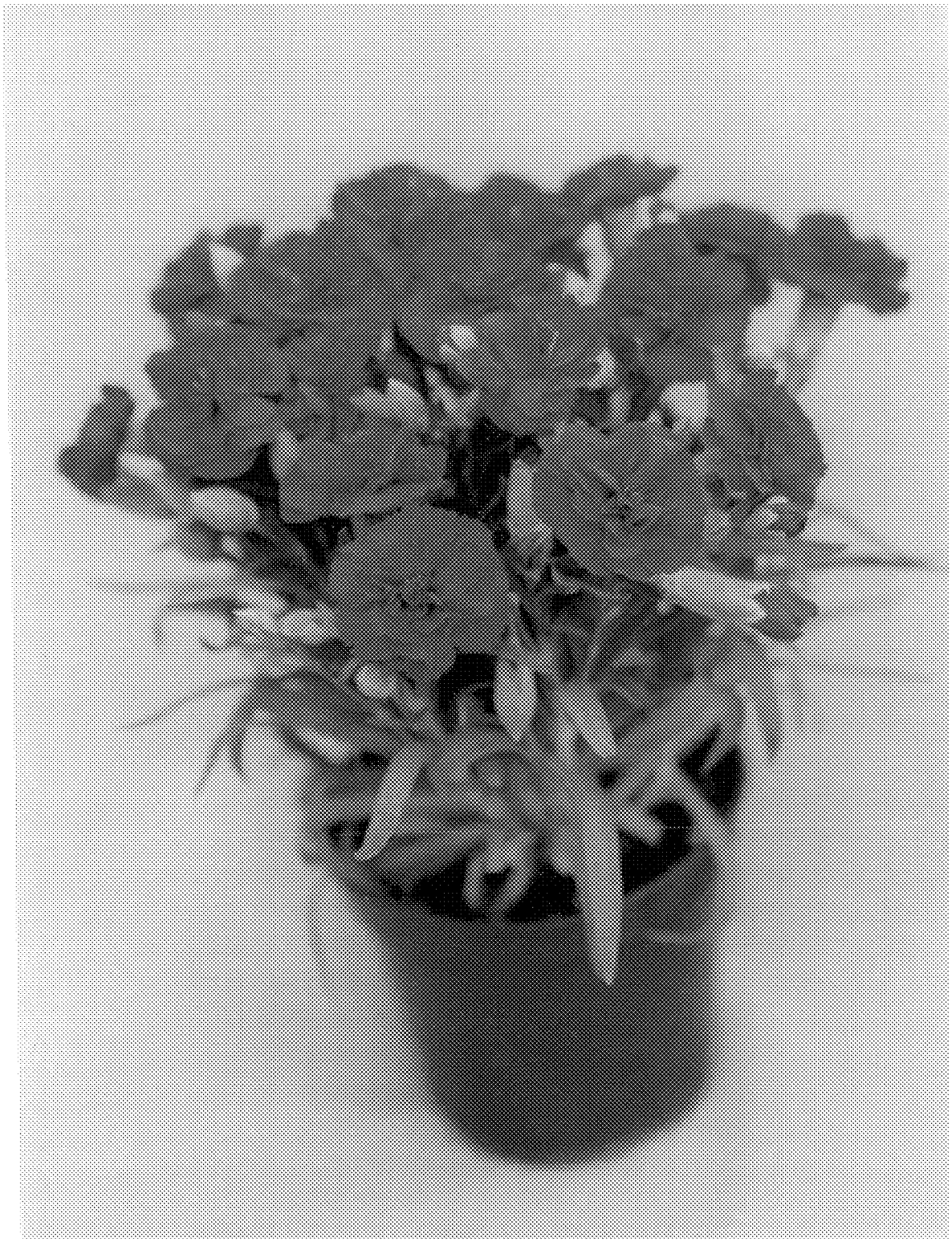

* * * * *